US00PP10641P

United States Patent [19]

Sonnoli, Jr.

[11] Patent Number: Plant 10,641

[45] Date of Patent: Oct. 13, 1998

[54] OLIVE TREE 'CSS 02 MINERVA-SONNOLI'

[76] Inventor: Attilio Sonnoli, Jr., Via Norfini 29, Pescia - PT, Italy

[21] Appl. No.: 757,029

[22] Filed: Nov. 26, 1996

[51] Int. Cl.[6] ..... A01H 5/00

[52] U.S. Cl. ..... Plt./33.1

[58] Field of Search ..... Plt./33.1

[56] References Cited

U.S. PATENT DOCUMENTS

| | | | |
|---|---|---|---|
| P.P. 1,521 | 9/1956 | Main | Plt./33.1 |
| P.P. 4,464 | 10/1979 | Wilson . | |
| P.P. 5,649 | 1/1986 | Herman . | |
| P.P. 6,266 | 8/1988 | Zylstra . | |

OTHER PUBLICATIONS

Sonnoli, "Minerva, Nuova Varietà Di Olivo," Terra e Vita, 11–17 Nov., 1995.

Anon. Listing for 'Minerva' *Plant Patent Directory* National association of Plant Patent Owners 1991, p. 0056.

GTITM UPOVROM–Listing for *Olea europaea* 'Minerva' US PLP 1521, Sep. 25, 1956.

GTITM Listing for *Olea europaea* 'Minervia' ITPBR 1047NV/1993 Name Proposed (Not accepted), May 29, 1993.

GTITM Listing for *Olea europaea* 'Minerva' AUPBR95244 (filing date), Nov. 8, 1995.

*Primary Examiner*—James R. Feyrer

*Attorney, Agent, or Firm*—Medlen & Carroll, LLP

[57] ABSTRACT

The present invention comprises a new and distinct selection of *Olea europea* L. (popularly known as an olive tree), hereinafter referred to as *Olea europaea* cultivar Minerva. *Olea europaea* differs distinctively from other olives due to its unique combination of its resistance to olive knot and cold temperatures, early entry into production, and its high yield of good quality oil with exceptional organoleptic qualities.

4 Drawing Sheets

DISCOVERY

The present invention relates to a new and distinct variety of olive tree. The plant was discovered by Attilio Sonnoli in 1956, at Pescara, in the Abruzzo Region of Central Italy. The seed parent of the new variety is an unpatented variety of *Olea europaea* known as "Leccino."

REPRODUCTION

The new variety has been asexually reproduced by Attilio Sonnoli at the location noted above in Italy, and L. Bazzani in Western Australia by means of cuttings. A large number of plants of the new variety have been reproduced by this method and in all cases, the resulting plants have exhibited the distinguishing characteristics of the parent plant, indicating that the new variety is established.

CHARACTERISTICS

Figure 1:
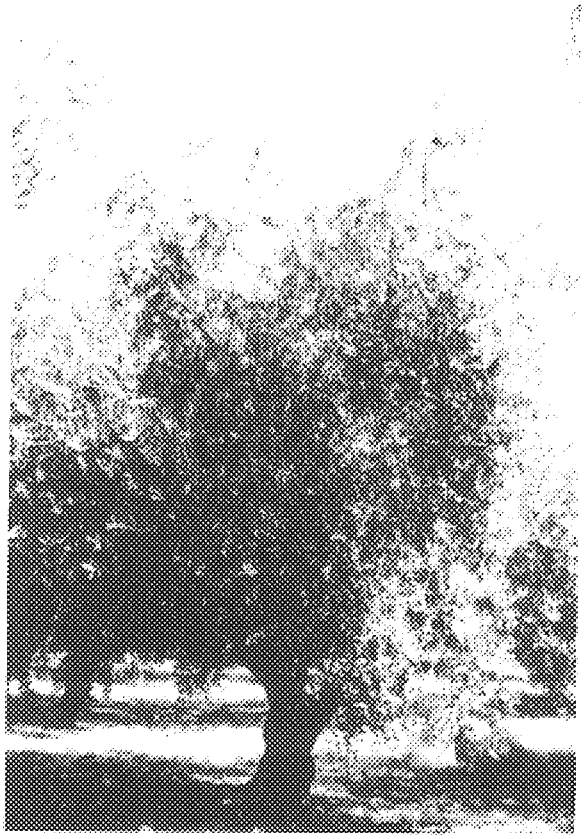
FIG. 1 is a photograph of a specimen of the new variety exhibiting its overall appearance.
Figure 2:
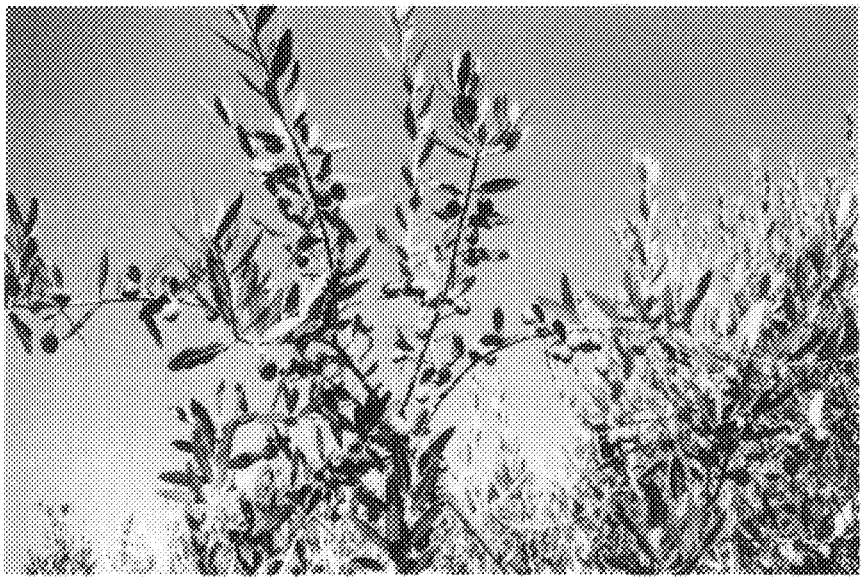
FIG. 2 is a photograph of a typical branch of the new variety bearing fruit.
Figure 3:
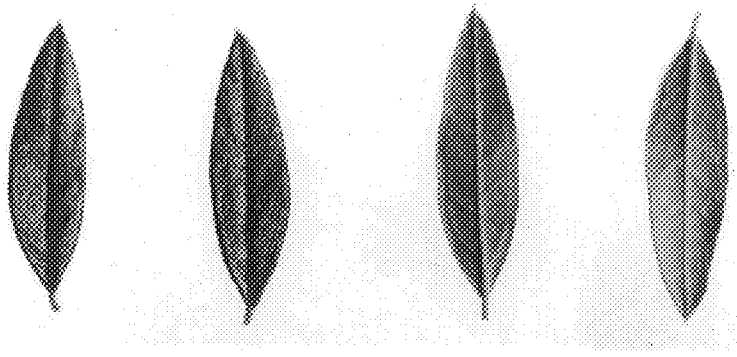
FIG. 3 is a photograph of life size leaves of the new variety showing the upper side (two left leaves) and lower side (two right leaves) of the leaves.

As compared with the "Leccino" variety, the new variety is characterized by its resistance to low temperatures, and resistance to olive knot (*Pseudomonas savastanoi*), and *Spilocea oleagina*. The leaves of the Leccino tree are green, while the leaves of the Minerva olive are more yellowish in color. The branches of the Minerva-Sonnoli tree are more prone to break off under the weight of snow than those of the Leccino tree. In addition, the Minerva-Sonnoli tree produces a greater yield of fruit, larger fruits, better oil quality, and higher frost resistance than the parent trees.

The erect posture of the trees make this variety suitable for mechanical harvest. The yield of oil is greater than the original variety, and is of higher quality. The new variety is also characterized by its early entry into production. The new variety is suitable for growth in cold and damp climates.

The cold hardiness of the Minerva-Sonnoli tree has been demonstrated through multiple frosts in Italy and New Zealand. For example, after the frosts of February, 1956 (−14° C.) and January 1995 (−20° C.), the Minerva-Sonnoli tree survived with only minor damage, while the other olive trees died. The same observation was made in New Zealand after the winter of 1997, during which the Minerva-Sonnoli tree was undamaged, while those of other varieties, including Barnea (Israeli variety), and Manzanilla (Spanish variety) as well as others were highly damaged or died.

In the first two or three years of growth, the precocity and productivity of the Minerva-Sonnoli tree are highly influenced by pruning. However, in comparison with Leccino, the yield of Minerva-Sonnoli has been consistently higher. In some areas, Minerva-Sonnoli is the first variety to be harvested. For example, in Tuscany, Minerva-Sonnoli is the first variety to harvest.

DESCRIPTION

Below is a detailed description of the new selection. The photographs closely approximate the colors of the tree, but to further facilitate the identification of the important colors, reference is made to The Royal Horticultural Society (R.H.S.) Colour Charts in the description of the new variety.

Tree:

*Size.*—The mature tree size is approximately 4 meters in height.

*Shape.*—The mature tree is erect, with a canopy of average size, with a spreading crown, that is globose in appearance. The canopy of mature trees is approximately 16–17 in diameter. The density of the canopy is average. Thus, the productivity is due to the higher fruit setting of Minerva-Sonnoli.

*Growth.*—Robust. The fruiting shoots are grey-green in color, similar to The R.H.S. colour chart colour designated as Greyed-Green Group 196A.

Wood:

*Surface texture.*—Smooth and does not vary with the age of the tree.

*Color.*—Yellowish green and does not vary with the age of the tree.

Leaves:

*Size.*—The leaves are approximately 40.5 mm in length and 13.02 mm in width, giving a length to width ratio of approximately 3.11.

*Shape.*—The leaves are elliptic and symmetrical. The transversal and longitudinal curvatures of the blade are flat. The apex and base angles are rounded. The margin of the leaves is complete. The venation of the leaves is palmate and conspicuous from the bottom of the leaf, but not the top. The top surface of the leaves is glabrous, while the bottom surface is matte.

*Color.*—The leaves are green in color, with the upper leaf color being similar to The R.H.S. colour chart colour designated as Green Group 139A, and the lower leaf color being similar to The R.H.S. colour chart color designated as Greyed-Green Group 195B.

*Arrangement.*—The leaves are opposite on the stem.

Flower:

*Season.*—The season of flowering in the Pescara province is approximately from the middle of May to the end of May. The reproductive organs of the flowers of Minerva-Sonnoli do not significantly differ from those of other olive species.

*Color.*—The color of the flower is creamy white.

Fruit:

*Weight.*—The fruit weight is approximately 3.4 g.

*Dimensions.*—The fruit length is approximately 21.6 millimeters, and the fruit width is approximately 16.4 millimeters. The fruit length to width ratio is approximately 1.3.

*Color.*—When ripe, the fruit is black to violet in color. The color is uniform.

*Shape.*—The fruit is elliptical in shape and symmetrical or slightly asymmetrical. The maximum diameter is measured at the center of the fruit. In cross-section, the fruit is circular in shape.

*Apex.*—Rounded.

Figure 4:
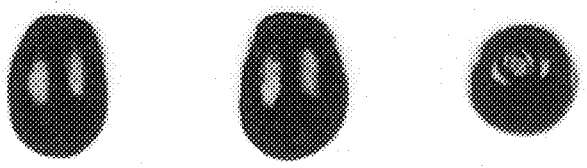
FIG. 4 is a photograph of life size ripe fruit of the new variety shown in side view (two left fruits) and top view (right fruit).
Figure 5:
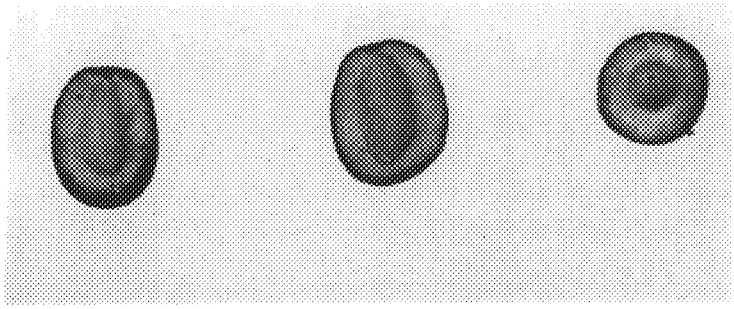
FIG. 5 is a photograph of a cross section of the fruit of the new variety shown in longitudinal cross section (two left fruits) and horizontal cross section (right fruit).
Figure 6:
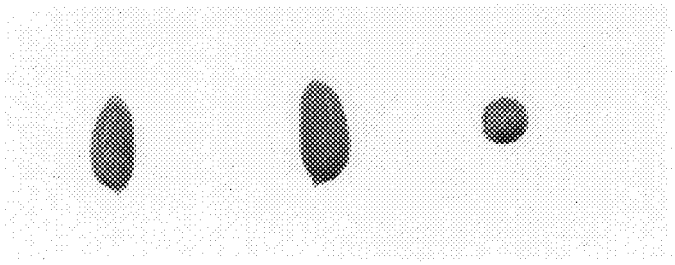
FIG. 6 is a photograph of the seeds of the new variety depicted in side view (two left seeds) and cross section (right seed).

*Base.*—In one orientation, the base is truncate. In an alternate orientation, the base is rounded (see FIG. 4).

*Umbo.*—Absent.

*Lenticels.*—Lenticels are not evident at the time of ripening.

Seed:

*Weight.*—The seed weight is approximately 0.54 grams.

*Dimensions.*—The seed length is approximately 15.65 millimeters, and the seed width is approximately 7.76 millimeters. The seed length to width ratio is approximately 2.01.

*Shape.*—The seed is elliptical in shape and slightly asymmetrical (See Figure . In cross-section, the seed is circular, with the largest cross-section being located centrally.

*Surface.*—Rugose.

*Grooves.*—The grooves are not uniform.

*Apex.*—Rounded.

*Base.*—Truncate.

*Mucron.*—Present.

*Suture.*—Marked.

Oil:

The oil yield is approximately 16–18% (weight/weight) when the fruit skin is firm black and the flesh is turgid and creamy light green.

While olive varieties are generally grown for one purpose (i.e., table olives and oil olives), the fruit of Minerva-Sonnoli tree is sufficiently large that it is suitable for table olive production, especially if the trees are irrigated. However, the major use of Minerva-Sonnoli is as an oil olive. The chemical analysis of two batches (November, 1989, and November 1993) of olive oil from Minerva-Sonnoli is shown in the table below. These results are for extra virgin oil, with a weak fruity flavor.

TABLE 1

Chemical Analysis of Minerva-Sonnoli Olive Oil

| Chemical | Date | |
|---|---|---|
| | November 1989 | November 1993 |
| Palmitic Acid | 13.4 | 12.02 |
| Palmitoleic Acid | 1.17 | 1.5 |
| Margaric Acid | — | 0.02 |
| Eptadecanoic Acid | — | 0.09 |
| Stearic Acid | 1.32 | 1.5 |
| Oleic Acid | 76.96 | 78.3 |
| Linoleic Acid | 6.98 | 4.0 |
| Linolenic Acid | 0.77 | 0.5 |
| Arachic Acid | 0.19 | 0.3 |
| Arachidonic Acid | 0.10 | — |

These analyses indicate the superior quality of the olive oil from fruit of the tree Minerva-Sonnoli.

I claim:

1. A new and distinct selection of *Olea europaea* tree as substantially shown and described herein, that is characterized particularly as being highly disease and cold resistant, and yielding high quality, organoleptic oil.

* * * * *